United States Patent
Traynor et al.

(10) Patent No.: US 7,025,952 B1
(45) Date of Patent: *Apr. 11, 2006

(54) METHODS OF PREPARATION AND USE OF BODYWASHES CONTAINING ADDITIVES

(75) Inventors: Daniel Henry Traynor, Sarasota, FL (US); Henry G. Traynor, Sarasota, FL (US); Steven M. Markowitz, Honolulu, HI (US); David L. Compton, Ventura, CA (US)

(73) Assignee: Aquea Scientific Corporation, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/076,088

(22) Filed: Mar. 8, 2005

Related U.S. Application Data

(60) Provisional application No. 60/648,961, filed on Jan. 31, 2005.

(51) Int. Cl.
*A61K 7/42* (2006.01)
*A61K 7/44* (2006.01)
*A61K 7/00* (2006.01)

(52) U.S. Cl. .................. 424/59; 424/60; 424/400; 424/401

(58) Field of Classification Search .............. 424/59, 424/60, 400, 401
See application file for complete search history.

(56) References Cited

U.S. PATENT DOCUMENTS

| | | | |
|---|---|---|---|
| 3,462,479 A | 8/1969 | Strobel et al. | |
| 4,540,507 A | 9/1985 | Grollier | |
| 4,542,125 A | 9/1985 | Gorman et al. | |
| 4,663,155 A | 5/1987 | Murray et al. | |
| 4,663,156 A | 5/1987 | Clum et al. | |
| 4,683,134 A | 7/1987 | Palinczar | |
| 4,686,099 A | 8/1987 | Palinczar | |
| 4,699,779 A | 10/1987 | Palinczar | |
| 4,701,321 A | 10/1987 | Bernstein | |
| 4,749,501 A | 6/1988 | Nakagawa et al. | |
| 4,803,195 A | 2/1989 | Holzner | |
| 4,874,538 A | 10/1989 | Dawson et al. | |
| 4,904,524 A | 2/1990 | Yoh | |
| 4,933,174 A | 6/1990 | Bernstein | |
| 4,985,170 A | 1/1991 | Dawson et al. | |
| 5,169,624 A | 12/1992 | Ziegler et al. | |
| 5,306,485 A | 4/1994 | Robinson et al. | |
| 5,455,048 A | 10/1995 | Lahmani et al. | |
| 5,476,660 A | 12/1995 | Somasundaran et al. | |
| 5,508,259 A | 4/1996 | Holzner et al. | |
| 5,543,136 A | 8/1996 | Aldous | |
| 5,589,177 A | 12/1996 | Herb et al. | |
| 5,661,189 A | 8/1997 | Grieveson et al. | |
| 5,674,912 A | 10/1997 | Martin | |
| 5,759,524 A | 6/1998 | Tanner et al. | |
| 5,770,556 A | 6/1998 | Farrell et al. | |
| 5,785,979 A | 7/1998 | Wells | |
| 5,849,273 A | 12/1998 | Bonda et al. | |
| 5,876,755 A | 3/1999 | Perring et al. | |
| 5,900,394 A | 5/1999 | Goel et al. | |
| 5,904,917 A | 5/1999 | Mattai et al. | |
| 5,948,416 A | 9/1999 | Wagner et al. | |
| 5,955,409 A | 9/1999 | Farrell et al. | |
| 5,989,529 A | 11/1999 | Kaplan | |
| 5,989,536 A | 11/1999 | Deckner et al. | |
| 6,024,942 A | 2/2000 | Tanner et al. | |
| 6,043,204 A | 3/2000 | Kaufman et al. | |
| 6,057,275 A | 5/2000 | Fair et al. | |
| 6,074,630 A | 6/2000 | Devillez et al. | |
| 6,096,697 A | 8/2000 | Wells | |
| 6,110,888 A | 8/2000 | Lupo, Jr. et al. | |
| 6,217,852 B1 | 4/2001 | Gildenberg et al. | |
| 6,224,852 B1 | 5/2001 | Morgan et al. | |
| 6,238,650 B1 * | 5/2001 | Lapidot et al. | ............... 424/59 |
| 6,248,703 B1 | 6/2001 | Finucane et al. | |
| 6,255,264 B1 | 7/2001 | Fleurot et al. | |
| 6,303,149 B1 | 10/2001 | Magdassi et al. | |
| 6,362,146 B1 | 3/2002 | Macaulay | |
| 6,391,287 B1 | 5/2002 | Baldo et al. | |
| 6,395,269 B1 | 5/2002 | Fuller et al. | |
| 6,399,045 B1 | 6/2002 | Morgan et al. | |
| 6,436,375 B1 | 8/2002 | Lapidot et al. | |
| 6,468,509 B1 | 10/2002 | Lapidot et al. | |
| 6,485,713 B1 | 11/2002 | Bonda et al. | |
| 6,500,791 B1 | 12/2002 | Pereira et al. | |
| 6,524,594 B1 * | 2/2003 | Santora et al. | ............... 424/401 |
| 6,555,095 B1 | 4/2003 | Garrison | |
| 6,576,228 B1 | 6/2003 | Crookham et al. | |
| 6,696,067 B1 | 2/2004 | Brandt et al. | |
| 6,699,824 B1 | 3/2004 | Dawson et al. | |

(Continued)

FOREIGN PATENT DOCUMENTS

EP 0025379 B1 6/1984

(Continued)

OTHER PUBLICATIONS

Eusolex® UV-Pearls™ Product Information http://www.emdchemicals.com/rona/Rona%20CP%20New%20s/Eusolex.pdf.

(Continued)

*Primary Examiner*—Shelley A. Dodson
(74) *Attorney, Agent, or Firm*—Wilson Sonsini Goodrich & Rosati

(57) ABSTRACT

The invention encompasses methods of use of bodywashes containing additive to modify skin, e.g., protection of skin from sunlight by application of a bodywash containing a sunscreen. Thus, in one aspect, the invention provides a method for protection of skin from sunlight by applying a bodywash comprising a sunscreen to the skin, where after application of the bodywash to skin and rinsing, the skin is protected from sunlight with an average SPF of at least about 15.

19 Claims, No Drawings

U.S. PATENT DOCUMENTS

| | | |
|---|---|---|
| 6,740,631 B1 | 5/2004 | Shefer et al. |
| 6,770,270 B1 | 8/2004 | Bonda |
| 6,825,161 B1 | 11/2004 | Shefer et al. |
| 2002/0028235 A1 | 3/2002 | Reed et al. |
| 2002/0034487 A1 | 3/2002 | Maubru et al. |
| 2002/0077256 A1 | 6/2002 | Niemiec et al. |
| 2003/0032593 A1 | 2/2003 | Wender et al. |
| 2003/0059382 A1 | 3/2003 | Brandt et al. |
| 2003/0059383 A1 | 3/2003 | SaNogueira et al. |
| 2003/0134761 A1 | 7/2003 | Sebillotte-Arnaud et al. |
| 2003/0147818 A1 | 8/2003 | Dubief et al. |
| 2003/0171230 A1 | 9/2003 | Shana'a et al. |
| 2003/0176303 A1 | 9/2003 | Niemiec et al. |
| 2004/0028709 A1 | 2/2004 | Dueva et al. |
| 2004/0101498 A1 | 5/2004 | Koshti et al. |
| 2004/0120905 A1 | 6/2004 | Gall et al. |
| 2004/0167046 A1 | 8/2004 | Lukenbach et al. |
| 2004/0234558 A1 | 11/2004 | O'Connor et al. |
| 2004/0247543 A1 | 12/2004 | Huerta et al. |
| 2005/0065047 A1 | 3/2005 | Shefer et al. |

FOREIGN PATENT DOCUMENTS

| | | |
|---|---|---|
| EP | 0254447 B1 | 3/1993 |
| EP | 0399911 B1 | 7/1993 |

OTHER PUBLICATIONS

Eusolex® UV-Pearls™ description page http://www.merck.de/servlet/PB/menu/1321870/.

Parsol® 1789 Product Page http://www.opotion.com/pages/parsol-what%20is.html.

Eusolex® T-AVO description page http://www.merck.de/servlet/PB/menu/1254730/.

U.S. Appl. No. 09/604,449, filed Jun. 27, 2000, Lukenbach et al.

* cited by examiner

METHODS OF PREPARATION AND USE OF BODYWASHES CONTAINING ADDITIVES

CROSS-REFERENCE

This application claims the benefit of U.S. Provisional Application No. 60/648,961 filed Jan. 31, 2005, which is incorporated herein by reference in its entirety.

BACKGROUND OF THE INVENTION

Exposure to ultraviolet light, primarily through exposure to the sun's rays, produces a number of harmful effects including premature skin aging, loss of elasticity, wrinkling, drying, and an increased risk of developing skin cancer. Currently a number of sunscreen products are marketed to protect against these harmful effects. All of these products contain agents known to filter out some of the sun's harmful rays incorporated into creams, ointments, lotions, solutions or suspensions. Such products are applied just prior to anticipated sun exposure, provide short term protection, and are removed by bathing, washing or normal desquamation of skin. Soap in the form of bodywash has for years been used to remove oil due to its surfactant composition and associated charges. A normal soap contains both charges of a positive and negative nature. Although attempts have been made to combine sunscreens with soaps (i.e., surfactant agents), none has provided an ideal combination of high sun protection factor (SPF) and long-lasting effect in a composition that maintains its integrity. Other additives in addition to sunscreen are also potentially useful when applied in conjunction with a bodywash, but at present few products utilize this potential. The current invention addresses these lacks.

SUMMARY OF THE INVENTION

The invention encompasses methods of use of bodywashes containing additive to modify skin, e.g., protection of skin from sunlight by application of a bodywash containing a sunscreen.

In one aspect, the invention provides a method for protection of skin from sunlight by applying a bodywash comprising a sunscreen to the skin, where after application of the bodywash to skin and rinsing, the skin is protected from sunlight with an average SPF of at least about 15. In some embodiments, the SPF of 15 is maintained for at least about 4 hours after rinsing. In some embodiments, the bodywash is applied at least twice, and in some of these embodiments, the average SPF after the second application of bodywash is greater than about 20. In some embodiments, the bodywash is applied about once per day. In some embodiments, the bodywash is applied more that about once per day. In some embodiments, the bodywash is applied about every other day. In some embodiments, the sunscreen is an organic sunscreen. In some embodiments, the bodywash contains an organic sunscreen and further contains an inorganic sunscreen. In some embodiments, the sunscreen is encapsulated, e.g., in sol-gel microcapsules. The bodywash may also contain a cationic polymer and/or a film former.

In another aspect, the invention provides a method for protection of skin from sunlight by applying a bodywash containing an additive that contains a sunscreen to the skin, where the sunscreen penetrates an average of no further than 30 microns into the skin after application followed by rinsing. In some embodiments, the sunscreen penetrates an average of no further than 50 microns into the skin after application followed by rinsing. In some embodiments, after application of the bodywash to skin and rinsing, the skin is protected from sunlight with an average SPF of at least about 15.

In a further aspect, the invention provides a method for protection of skin from sunlight by applying a bodywash to the skin, where the bodywash contains a UVA-absorbing sunscreen, a UVB-absorbing sunscreen, a physical blocker sunscreen, and a cationic polymer. In some embodiments, the UVB-absorber sunscreen is selected from the group consisting of aminobenzoic acid, cinoxate, dioxybenzone, homosalate, octocrylene, octyl methoxycinnamate, octyl salicylate, oxybenzone, padimate O, phenylbenzimidazole sulfonic acid, sulisobenzone, and trolamine salicylate; the UVA-absorber sunscreen is selected from the group consisting of avobenzone and menthyl anthranilate; the physical blocker sunscreen is selected from the group consisting of titanium dioxide and zinc oxide; and the cationic polymer is a polyquaternium. In some embodiments, at least one of the sunscreens is encapsulated, e.g., in a sol-gel microcapsule. In some embodiments, the physical blocker sunscreen is coated with silica. In some embodiments, the cationic polymer is a polyquaternium. In some embodiments, the bodywash further contains a film former and/or a non-sunscreen active.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention encompasses compositions containing one or more active ingredients (also referred to herein as "actives") that may be added to a bodywash composition to provide an active/bodywash combination. The invention also encompasses a bodywash containing such an active ingredient. In some embodiments, the active ingredient is one or more sunscreens. The invention further encompasses methods of use and manufacture of the compositions, and business methods.

As used herein, "bodywash" encompasses all cleansing vehicles applied to the body. Exemplary forms of cleansing vehicles include, but are not limited to, liquid, bar, gel, foam, aerosol or pump spray, cream, lotion, stick, powder, or incorporated into a patch or a towelette. In addition, soapless cleansers may be used as well. The bodywash can be made into any suitable product form. Thus, as used herein, "bodywash" includes, but is not limited to, a soap including liquid and bar soap; a shampoo; a hair conditioner; a shower gel; including an exfoliating shower gel; a foaming bath product (e.g. gel, soap or lotion); a milk bath; a soapless cleanser, including a gel cleanser, a liquid cleanser and a cleansing bar; moist towelettes; a body lotion; a body spray, mist or gel; bath effervescent tablets (e.g., bubble bath); a hand and nail cream; a bath/shower gel; a shower cream; a depilatory cream; a shaving product e.g. a shaving cream, gel, foam or soap, an after-shave, after-shave moisturizer; and combinations thereof, and any other composition used for cleansing or post-cleansing application to the body, including the skin and hair. Especially useful as bodywashes in the invention are soaps, e.g., liquid soaps and bar soaps, and shampoos.

I. Compositions

In one aspect, the invention provides additives containing active ingredients, where the additive is designed to be added to a bodywash (e.g., soap or shampoo). In some embodiments, the invention provides sunscreen compositions ("sunscreen additives") that may be added to a bodywash preparation to impart sun protection. In some embodiments, the invention provides a combination of a sunscreen additive and a bodywash preparation ("sunscreen/bodywash"). Thus, a sunscreen additive of the invention may be mixed with a conventional bodywash; alternatively, the invention provides pre-mixed sunscreen/bodywash. In either case, the sunscreen/bodywash composition is generally applied in the same manner as the bodywash alone and, typically, rinsed, with additive, e.g., sunscreen protection, being left on the skin after rinsing. In some cases, e.g., soapless cleansers, the bodywash is applied without rinsing. For sunscreen additives as part of a sunscreen/bodywash, the sunscreen protection after application and, typically, rinsing is, on average, greater than an SPF of 1, up to about SPF 50. As used herein in the context of SPF, "average SPF" is the SPF, determined as described herein, for about 5 to about 50 subjects, or about 5 to about 20 subjects, or about 5 to about 10 subjects, where the subjects preferably have Type II skin. In some embodiments, the average SPF provided by the sunscreen/bodywash after rinsing is about 1 to about 50, or about 2 to about 50, or about 2 to about 40, or about 2 to about 30, or about 2 to about 20, or about 2 to about 10, or about 2 to about 5, or about 5 to about 25, or about 5 to about 20, or about 5 to about 15, or about 5 to about 10. In some embodiments, the average SPF provided by the sunscreen/bodywash, after rinsing, is above about 1, 2, 3, 4, 5, 6, 7, 8, 9, 10, 11, 12, 13, 14, 15, 16, 17, 18, 19, or 20. In some preferred embodiments, the average SPF after rinsing is above about 2. In some preferred embodiments, the average SPF after rinsing is above about 5. In some preferred embodiments, the average SPF after rinsing is above about 10. In some preferred embodiments, the average SPF after rinsing is above about 15. In some embodiments, the average SPF provided by the sunscreen/bodywash of the invention remains above about 1, 2, 3, 4, 5, 6, 7, 8, 9, 10, 11, 12, 13, 14, 15, 16, 17, 18, 19, or 20, for an average of at least about 0.5, 1, 2, 3, 4, 5, 6, 7, 8, 9, 10, or more than about 10 hours after rinsing. In some embodiments the average SPF provided by the sunscreen/bodywash of the invention increases with each additional washing after a first wash, so that after a second, third, fourth, or fifth wash, the SPF provided can be above about 2, 4, 6, 8, 10, 15, 20, 25, 30, 40, 45, or more than about 45.

SPF is a commonly used measure of photo protection of a sunscreen against erythema. This number is derived from another parameter, the minimal erythemal dose (MED). MED is defined as the "least exposure dose at a specified wavelength that will elicit a delayed erythema response." The MED indicates the amount of energy irradiating the skin and the responsiveness of the skin to the radiation. The SPF of a particular photo protector is obtained by dividing the MED of protected skin by the MED of unprotected skin. The higher the SPF, the more effective the agent in preventing sunburn. The SPF value tells how many times longer a person can stay in the sun before the person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. Typically, commercially available sunscreening products have SPF values ranging from about 2 to 45.

Methods for measuring SPF are described in, e.g., FDA monograph C.F.R. 21. A method for applying the sunscreen prior to measurement is as follows: Wet 50 $cm^2$ square area of testing site with 10 ml of water delivered with a syringe. Apply test sample as per FDA monograph to area. Work lather on the subject for 3 minutes to allow the product to absorb into the skin. Rinse area after 2 additional minutes with 20 ml of water. Pat dry and allow 15 minutes before exposure to radiation as per FDA monograph.

In some embodiments, after application of the bodywash containing the additive (e.g., sunscreen) to the skin followed by rinsing, the additive (e.g., sunscreen) penetrates to an average of at least about 5 microns beneath the skin surface. In some embodiments, the additive penetrates to an average of at least about 10, 15, 20, 25, 30, 40, 50, 60, 70, 80, 90, 100, 120, or 150 microns beneath the skin surface. In some embodiments, after application of the bodywash containing the additive (e.g., sunscreen) to the skin followed by rinsing, the additive (e.g., sunscreen) penetrates to an average of no more than about 30 microns beneath the skin surface. In some embodiments, the additive penetrates to an average of no more than about 50, 40, 30, 25, 20, 15, 10, or 5 microns beneath the skin surface. In some embodiments, after application of the bodywash containing the additive (e.g., sunscreen) to the skin followed by rinsing, the additive (e.g., sunscreen) penetrates to an average of about 5 to about 50, or about 5 to about 40, or about 5 to about 30, or about 10 to about 40, or about 15 to about 40, or about 20 to about 40, or about 5, 10, 15, 20, 25, 30, 25, 40, 45, or 50 microns beneath the skin surface. Depth of penetration may be tested by tape stripping methods, as are well-known in the art.

The sunscreen additives and sunscreen/bodywashes of the invention contain at least one sunscreen. In some embodiments, the sunscreen additives of the invention contain one, two, three, four, or more than four sunscreens. In preferred embodiments, the sunscreen additives of the invention include three sunscreens. In other preferred embodiments, the sunscreen additives of the invention include four sunscreens. The sunscreens may be organic or inorganic. The sunscreens may be a UVA absorber, a UVB absorber, a physical blocker, or any combination thereof. In some embodiments one or more of the sunscreens is encapsulated. A number of types of encapsulation may be employed as described herein.

Compositions of the invention may include one or more actives that are not sunscreens, where the composition is designed to be an additive to a bodywash. In some compositions of the invention, the actives are provided in combination with one or more sunscreens. In some compositions, the actives are provided without sunscreen.

The additives, e.g., sunscreen additives, and additive/bodywashes, e.g., sunscreen/bodywashes, of the invention may further include one or more components to provide a positive charge to the system to assist with attachment to protein and other charged components of skin and/or hair, e.g., cationic polymeric agents. The cationic polymer may be, for example, a quaternium, e.g., polyquaternium.

The additives, e.g., sunscreen additives, and additive/bodywashes, e.g., sunscreen/bodywashes, of the invention may further include a film former.

Other optional ingredients of the additives, e.g., sunscreen additives, and additive/bodywashes, e.g., sunscreen/bodywashes, of the invention include preservatives, antioxidants, chelating agents, liquid hydrocarbon (e.g., similar to pentane), foaming agents (e.g., a cationic foaming agent), skin nourishing components, antibacterials, medicinals, and the like, as described below.

The additives, e.g., sunscreen additives, of the invention may be combined with any conventional bodywash. The bodywash composition with which the additive, e.g., sunscreen additive is combined may be any bodywash known in the art or apparent to one of skill in the art, as described above. In embodiments where the additive is a non-sunscreen active, the additive may be combined with any composition intended for topical application. In these embodiments, the additive is often encapsulated, e.g., in sol-gel microcapsules.

In some embodiments the invention provides an additive, e.g., sunscreen additive, in combination with a bodywash composition to provide an additive/bodywash, e.g. sunscreen/bodywash, composition. In these embodiments, the additive, e.g., sunscreen additives, of the invention are provided in combination with one or more surfactants. The surfactant(s) may be cationic, anionic, nonionic, zwitterionic, amphoteric, or any combination thereof. In preferred embodiments, the sunscreen/bodywash compositions of the invention include at least one cationic surfactant.

A. Sunscreens

The sunscreen additives and sunscreen/bodywashes of the invention contain at least one sunscreen. The sunscreen may be organic or inorganic, or a combination of both may be used. Sunscreens of use in the invention include UV absorbers or blockers (e.g., many inorganic sunscreens are UV blockers). UV absorbers may be a UVB or UVA absorber (e.g., UVA I or UVA II absorber). In some embodiments, the sunscreen additives or sunscreen/bodywashes of the invention include an organic and an inorganic sunscreen. In some embodiments, the sunscreen additives or sunscreen/bodywashes of the invention include more than one organic sunscreen (e.g., at least one UVB absorber and at least one UVA absorber) and at least one inorganic sunscreen. In some embodiments, the sunscreen additives of the invention include only a physical blocker sunscreen, e.g., titanium dioxide. These embodiments may further contain a cationic polymer and/or a film former, as well as any other components described herein for sunscreen additives.

Additional ingredients may include film formers, cationic polymers, antioxidants, preservatives, and the like, as described herein. In some embodiments, the sunscreen additives or sunscreen/bodywashes of the invention include an organic and an inorganic sunscreen. In some embodiments, the sunscreen additives or sunscreen/bodywashes of the invention include more than one organic sunscreen (e.g., at least one UVB absorber and at least one UVA absorber) and at least one inorganic sunscreen.

In preferred embodiments, one or more of the sunscreens used in the invention are encapsulated.

Any sunscreen known in the art or apparent to the skilled artisan may be used in the invention. The term "sunscreen" or "sunscreen agent" as used herein defines ultraviolet ray-blocking compounds exhibiting absorption or blockage within the wavelength region between about 290 and 420 nm. Sunscreens may be classified into five groups based upon their chemical structure: para-amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide and polymer particles such as those of polyethylene and polyamides.

Specific suitable sunscreens include, for example: p-aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropylene glycol esters); Cinnamic acid derivatives (methyl and benzyl esters, alpha-phenyl cinnamonitrile; butyl cinnamoyl pyruvate); Dihydroxycinnamic acid derivatives (umbelliferone, methylumbelliferone, methylacetoumbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,3-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenlyll); Diazoles (2-acetyl-3-bromoindazole, phenyl benzoxazole, methyl naphthoxalole, various aryl benzothiazoles); Quinine salts (bisulfate, sulfate, chloride, oleate, and tannate); quinoline derivatives (8-hydroxyquinoline salts, 2-phenylquinoline); Hydroxy- or methoxy substituted benzophenones; Uric and vilouric acids; Tannnic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy4,4'-dimethoxybenzophenone, Octabenzone; 4-Isopropylbenzoylmethane; Butylmethoxydibenzoylmethane; Etocrylene; and 4-isopropyl-di-benzoylmethane; titanium dioxide, iron oxide, zinc oxide, and mixtures thereof. Other cosmetically-acceptable sunscreens and concentrations (percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

In preferred embodiments, sunscreens are FDA-approved or approved for use in the European Union. For example, FDA-approved sunscreens may be used, singly or, preferably, in combination. See, e.g., U.S. Pat. Nos. 5,169,624; 5,543,136; 5,849,273; 5,904,917; 6,224,852; 6,217,852; and Segarin et al., chapter Vil, pages 189 of Cosmetics Science and Technology, and Final Over-the-Counter Drug Products Monograph on Sunscreens (Federal Register, 1999:64:27666–27963), all of which are incorporated herein by reference.

For example, for a product marketed in the United States, preferred cosmetically-acceptable sunscreens and concentrations (reported as a percentage by weight of the total cosmetic sunscreen composition, and referring to the final percentage of the sunscreen after addition to the bodywash) include: aminobenzoic acid (also called para-aminobenzoic acid and PABA; 15% or less; a UVB absorbing organic sunscreen), avobenzone (also called butyl methoxy dibenzoylmethane; 3% or less, a UVA I absorbing organic sunscreen), cinoxate (also called 2-ethoxyethyl p-methoxycinnamate; 3% or less, a UVB absorbing organic sunscreen), dioxybenzone (also called benzophenone-8; 3% or less, a UVB and UVA II absorbing organic sunscreen), homosalate (15% or less, a UVB absorbing organic sunscreen), menthyl anthranilate (also called menthyl 2-aminobenzoate; 5% or less, a UVA II absorbing organic sunscreen), octocrylene (also called 2-ethylhexyl-2-cyano-3,3 diphenylacrylate; 10% or less, a UVB absorbing organic sunscreen), octyl methoxycinnamate (7.5% or less, a UVB absorbing organic sunscreen), octyl salicylate (also called 2-ethylhexyl salicylate; 5% or less, a UVB absorbing organic sunscreen), oxybenzone (also called benzophenone-3; 6% or less, a UVB and UVA II absorbing organic sunscreen), padimate 0 (also called octyl dimethyl PABA; 8% or less, a UVB absorbing organic sunscreen), phenylbenzimidazole sulfonic acid (water soluble; 4% or less, a UVB absorbing organic sunscreen), sulisobenzone (also called benzophenone-4; 10% or less, a UVB and UVA II absorbing organic sunscreen), titanium dioxide (25% or less, an inorganic physical blocker of UVA and UVB), trolamine salicylate (also called triethanolamine salicylate; 12% or less, a UVB absorbing organic sunscreen), and zinc oxide (25% or less, an inorganic physical blocker of UVA and UVB).

For a product marketed in the European Union, preferred cosmetically-acceptable photoactive compounds and concentrations (reported as a percentage by weight of the total cosmetic sunscreen composition, and referring to the final percentage of the sunscreen after addition to the bodywash) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), octyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine. (10% or less, also called TINOSORB S).

In some embodiments, the sunscreen additives or sunscreen/bodywashes of the invention include a silicone long-chain molecule with chromophores, e.g., PARASOL SLX (DSM Nutritional Products), which contains benzyl malonate chromophores attached to specific points on a polysiloxane chain. Thus, in some embodiments, the invention provides a sunscreen additive or sunscreen/bodywash composition that contains sunscreen that comprises a silicone long-chain molecule with chromophores. For example, compositions of the invention include a composition containing octyl methoxycinnamate, octocrylene, avobenzone, titanium dioxide, and a silicone long-chain molecule with chromophores. The silicon long-chain molecule may be used in sunscreen additives at about 0.5 to about 5%, or in sunscreen/bodywashes at about 0.2 to about 2%.

Inorganic physical blockers of UVA and UVB useful in the invention further include iron oxide and polymer particles such as those of polyethylene and polyamides.

In some embodiments, the sunscreen additives and sunscreen/bodywashes contain at least one sunscreen active that is cinnamate (e.g., Octylmethoxycinnamate (ethyl hexyl methoxycinnamate), (available under the tradename PARSOL MCX), oxybenzone (e.g., benzophenone-3 (2-Hydroxy4-Methoxybenzophenone), avobenzone (4-tert-Butyl-4'-methoxydibenzoylmethane or PARSOL 1789), octyl salicylate (2-Ethylhexyl Salicylate), octocrylene (2-Ethylhexyl 2-Cyano-3,3-Diphenylacrylate), methyl anthranilate, and/or titanium dioxide, or combinations thereof.

Sunscreen additives and sunscreen/bodywashes of the invention may, in some embodiments, contain as a sunscreen component only titanium dioxide. When titanium dioxide is used in compositions of the invention, either alone or in combination with other sunscreens, the titanium dioxide can have an anatase, rutile, or amorphous structure. The titanium dioxide particles can be uncoated or can be coated with a variety of materials including, but not limited to, aluminum compounds such as aluminum oxide, aluminum stearate, aluminum laurate and the like; phospholipids such as lecithin; silicone compounds; and mixtures thereof. Various grades and forms of titanium dioxide are described in CTFA Cosmetic Ingredient Dictionary, Third Edition (1982), pp. 318–319; U.S. Pat. No. 4,820,508 to Wortzman, issued Apr. 11, 1989; and World Patent No. WO 90/11067 to Elsom et al, published Oct. 4, 1990; these three references are incorporated by reference herein in their entirety. Suitable grades of titanium dioxide for use in the compositions of the present invention are available commercially such as the MT micronized series from Tri-K Industries (Emerson, N.J.). These micronized titanium dioxides generally have a mean primary particle size ranging from about 10 nm to about 50 nm. For example, titanium dioxide having a mean primary particle size of about 15 nm is available under the trade designations MT-15OW (uncoated) and MT-100T (coated with stearic acid and aluminum compounds). Uncoated titanium dioxides having mean primary particle sizes of around 35 nm and around 50 nm are available under the trade designations MT-500B and MT-600B, respectively. Other coated titanium dioxides having a mean primary particle size around 15 nm include MT-100F (modified with stearic acid and iron hydroxide) and MT-100S (treated with lauric acid and aluminum hydroxide). Mixtures of two or more types and particle size variations of titanium dioxide can be used in the present invention.

A particularly preferred form of titanium dioxide is silica-coated $TiO_2$. Such a silica-coated $TiO_2$ is available under the tradename T-AVO (Eusolex).

If a zinc compound is chosen as the inorganic sunscreen, some zinc-based compositions (e.g., Z-Cote™ HP 1 [registered trademark, SkinCeuticals]) provide micro-fine zinc oxide coated with a form of dimethicone. As expressed by the manufacturer, the dimethicone coating transforms the frequently granular and pasty particles of zinc oxide to a smooth formulation which is transparent. The micronizing of these particles achieves the important advantage of providing effective sunscreening without giving the appearance of skin coated with white paint.

Also to be noted in relation to inorganic blockers are Tioveil and Spectraveil (both of the Tioxide Group). Tioveil include products which are 40% dispersions of surface-treated titanium dioxide in a range of cosmetic vehicles. Spectraveil include products which are 60% dispersions of zinc oxide in a range of cosmetic vehicles. In certain variations, these products may be film-formers and may have advantageous uses here.

In sunscreen additives, the total sunscreens comprise about 0.1–50%, or about 1–30%, or about 1–25%, or about 3–25%, or about 5–25%, or about 10–25% or about 15–25%, or about 5, 10, 15, 20, 25, 30, 35, 40, 45, or 50% of the composition (all percentages herein are weight percent unless otherwise specified). In sunscreen/bodywash compositions, the total sunscreens can comprise 0.05–30%, or about 0.5–15%, or about 0.5–12%, or about 1.5–12%, or about 2.5–12%, or about 5–12% or about 7–12%, or about 2.5, 5, 7.5, 10, 12.5, 15, 20, 25, 30, 33, 35, 40, 45, 50, or more than 50% of the composition.

In some embodiments, a sunscreen additive of the invention includes octyl methoxycinnamate at about 4.5–9%, Octocrylene at about 0.5–15%, Avobenzone (e.g., PARSOL 1789) at about 2–4%, and titanium dioxide at about 3–9%. In some embodiments, the octyl methoxy cinnamate is encapsulated, e.g., in amorphous silica. Such encapsulated octyl methoxy cinnamate is commercially available under the trade name UV PEARLS; about 20–40% UV PEARLS supplies about 4.5–9% octyl methoxy cinnamate. In some embodiments, a sunscreen additive of the invention includes octyl methoxycinnamate at about 7.6% (in some embodiments, encapsulated as described, e.g., in UV PEARLS wherein the UV PEARLS are provided at about 33.3%), Octocrylene at about 11.3%, Avobenzone (PARSOL 1789) at about 2.8%, and titanium dioxide at about 6.4%. The sunscreen additives may further include a polyquaternium, e.g., polyquaternium-4. In some embodiments, the polyquaternium-4 is present at about 0.5% to about 5%, in some embodiments, the polyquaternium-4 is present at about 2.8%. The sunscreen additives may further include a film-former, which may comprise dimethicone and/or petrolatum, and/or a preservative, such as BHT. This sunscreen additive may be added to a conventional bodywash formulation (e.g., SUAVE Bodywash) in a ratio of about one part sunscreen additive to two parts bodywash (w/w). Other ratios are encompassed by the invention, e.g., about one part sunscreen additive to about 0.2, 0.5, 0.7 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10; 12, 15, or 20 parts bodywash (w/w).

It will be appreciated by those of skill in the art that the various ingredients of the sunscreen additive may be added to the bodywash all at once, or in groups, or separately. In some embodiments, the sunscreen additive comprises at least two components. For example, the first component may comprise all the ingredients except an inorganic or physical blocker sunscreen, and the second component may comprise the inorganic or physical blocker sunscreen. The first component is added to the bodywash with thorough mixing, then the second component is added. For example, in some embodiments, all ingredients except the titanium dioxide are mixed, then added to the bodywash, and then the titanium dioxide is added (see Examples).

In some embodiments, the sunscreen additives of the invention include about 0.1 to 7.5 weight percent of octyl-methoxy cinnamate, about 0.1 to 6 parts weight percent of octyl salicylate, about 0.1 to 5 parts weight percent of oxybenzone, about 1 to 10 weight percent of cationic surfactant, and about 0.01 to 1 weight percent of a quaternized compound. These composition may further include a film former. These compositions may further include 0.01 to 1 weight percent of a preservative.

Encapsulation Sunscreens and other actives used in the invention may be encapsulated. One or more of the sunscreens used in a composition may be encapsulated; preferably, all sunscreens used are encapsulated. Sunscreen actives may be encapsulated together, or may be encapsulated separately, in any combination, in the same or in different types of encapsulations. Generally, encapsulation involves trapping the sunscreen in, e.g., a vesicle. Depending on the vesicle of choice, the vesicle may break open when applied. Without being limited by theory, it is thought that the vesicle breaks open in various types of encapsulation due to friction, temperature, or pH from the skin or hair, or some combination of these. By choosing the appropriate capsule and additives for the system, the stability, durability, and/or SPF provided by the sunscreen additives and sunscreen/bodywashes of the invention can be increased.

Any means of encapsulation known in the art, including but not limited to liposomes, maltodextrin capsules, silica gels, siloxanes, and the like, may be used in the compositions of the invention. A cationic or catanionic in dry powder form may also be used to encapsulate sunscreen. Commercial embodiments of encapsulated sunscreens or vehicles suitable for encapsulating sunscreens include CATEZOMES (Engelhard Corp.), EUSOLEX UV PEARLS (EMD Biosciences), and others known in the art. Methods of encapsulation suitable for delivering benefit agents that are mixed with a bodywash composition are well-known in the art. See, e.g., U.S. Pat. Nos. 6,825,161; 6,436,375; 6,238,650; 6,468,509, 6,362,146; 6,074,630; 5,455,048; 5,770,556; 5,955,409; 5,876,755; 4,803,195; 5,508,259; 4,749,501; 6,248,703; 5,476,660; and 4,904,524 and EP Pat. Nos. 0,254,447; 0,025,379; and 0,399,911.

A particularly preferred method of encapsulation is sol-gel encapsulation. This technique is described in, e.g., U.S. Pat. Nos. 6,238,650; 6,436,375, 6,303,149; and 6,468,509. Any or all of the sunscreens and/or other active ingredients of the compositions of the invention may be encapsulated by such sol-gel encapsulation. The sol-gel capsules may be prepared so as to have a surface charge, e.g., a cationic charge. This is advantageous in that otherwise water-insoluble components may be encapsulated within the microcapsules, which are then freely miscible in water, e.g., without the need for an emulsifying agent: For example, in some embodiments, a UVA absorber, a UVB absorber (e.g., octyl methoxycinnamate) and/or a physical blocker, e.g., titanium dioxide, is provided as a silica sol-gel encapsulate, optionally with further ingredients including PVP, Chlorphenesin, and an antioxidant such as BHT. A commercial embodiment of such an encapsulation containing octyl methoxycinnamate, PVP, chlorphenesin, and BHT, is available under the trade name EUSOLEX UV PEARLS (EMD Biosciences). Such a silica sol-gel encapsulated UVB absorber, e.g., octyl methoxycinnamate, may be used in a sunscreen additive at a concentration that results in a final concentration of the UVB absorber of about 1% to about 40%, or about 2% to about 20%, or about 2% to about 10%, or about 5% to about 10%, or about 6%, 7%, 7.4%, 7.5%, 7.6%, 8%, or 9%. The preferred final concentration is about 7.6%. In other embodiments, more than one sunscreen is encapsulated as silica sol-gel encapsulate. In these embodiments, the final concentration of each of the sunscreens, independently, in the final sunscreen additive, is about 1% to about 40%, or about 2% to about 20%, or about 2% to about 10%, or about 1%, 2%, 3%, 4%, 5%, 6%, 7%, 7.5%, 8%, 9%, or 10%. The sunscreens may be encapsulated together or separately, or any combination thereof. In some embodiments, the invention provides an additive for addition to a bodywash that includes a sunscreen encapsulated in a sol-gel microcapsule and a cationic polymer (described below). Further ingredients in these embodiments may include a film former, antioxidant, preservative, chelating agent, thickener, emollient, and/or other active and inactive ingredients as described herein.

In some embodiments wherein encapsulation, e.g., sol-gel microencapsulation, is utilized, the composition of the microcapsule, e.g., sol-gel microcapsule, may be varied so as to allow for varying amounts of the active, e.g., sunscreen, within the microcapsule to be released. The microcapsules, e.g., sol-gel microcapsules, can be prepared so as to experience no or minimal breakage when applied to the skin and when left on the skin. Alternatively, the microcapsules, e.g., sol-gel microcapsules, can be prepared so as to experience various degrees of breakage, on average, when applied to the skin and when left on the skin. Thus, the microcapsules, e.g., sol-gel microcapsules, may be prepared so as to experience about 0% breakage, or breakage in a range from about 0.1, 0.5, 1, 2, 5, 10, 20, 30, 40, 50, 60, 70, 80, or 90% to about 0.5, 1, 2, 5, 10, 20, 30, 40, 50, 60, 70, 80, or 90%, after application (or application and rinsing in the case of a or bodywash containing the microcapsules). Furthermore, the microcapsules may be formulated so as to break open in response to conditions that occur on the skin, so that after application the microcapsules act to release their contents in a time-release or controlled manner. Non-limiting exemplary skin or hair conditions that can vary with the user's environment, the variation of which can trigger breakage of microcapsules, include pH, temperature, friction, exposure to light or air, pressure, and the like.

Other forms of immobilization or entrapment of sunscreen and other active components are also useful. For example, as a further variant of the use of chemical sunscreen agents, compositions of the invention may employ an organic sunscreen such as octyl methoxycinnamate trapped within a matrix. A commercial example of such a composition is found in SunCaps™ (trademark, SkinCeuticals) in which the organic sunscreen molecules are evenly distributed throughout the particle.

B. Non-sunscreen Actives

In one aspect, the invention provides additives containing non-sunscreen active ingredients, where the additive is designed to be added to a composition for topical application, e.g., a bodywash. These actives may be used in combination with the sunscreens described above in a sunscreen additive or sunscreen/bodywash, or may be used in separate, non-sunscreen compositions. In some embodiments, at least one of the actives is encapsulated. In another aspect, the invention provides a composition for topical application, e.g., a bodywash, containing one or more such actives. These actives may be used in combination with the sunscreens described above in a sunscreen additive or sunscreen/bodywash, or may be used in separate, non-sunscreen compositions.

Non-limiting examples of non-sunscreen actives useful in compositions of the invention include sunless tanning actives, skin lightening actives, anti-acne actives, anti-skin wrinkling and anti-skin aging actives, vitamins, anti-inflammatory actives, anesthetic actives, analgesic actives, antipruritic actives, anti-microbial actives (e.g. antifungals, antibacterials, and antiparasitics), anti-virals, anti-allergenics, medicinal actives (e.g., skin rash, skin disease and dermatitis medications), anti-cellulite additives, insect repellant actives, antioxidants, hair growth promoters, hair growth inhibitors, hair bleaching agents, deodorant compounds, and mixtures and combinations thereof.

Sunless tanning actives include dihydroxyacetone (DHA); glyceryl aldehyde; tyrosine and tyrosine derivatives such as malyltyrosine, tyrosine glucosinate, and ethyl tyrosine; phospho-DOPA, indoles and derivatives; and mixtures thereof.

Non-limiting examples of skin lightening actives include EMBLICA (also an antioxidant), monobenzone (a depigmenting agent), kojic acid, arbutin, ascorbic acid and derivatives thereof (e.g., magnesium ascorbyl phosphate or sodium ascorbyl phosphate), and extracts (e.g., mulberry extract, placental extract). Non-limiting examples of skin lightening agents suitable for use herein also include those described in WO 95/34280, WO 95/07432, and WO 95/23780.

Vitamins may be included in the compositions of the present invention. Examples include Vitamin A and derivatives thereof (including, for example, retinol, see anti-wrinkling actives), ascorbic acid (Vitamin C and derivatives), Vitamin B (e.g., riboflavin, vitamin $B_2$), biotin, Vitamin D (all forms), Vitamin E and derivatives thereof such as tocopheryl acetate, beta-carotene, panthothenic acid and mixtures thereof.

Anti-acne actives include benzoyl peroxide, erythromycin, clindamycin phosphate, 5,7-dichloro-8-hydroxyquinoline, resorcinol, resorcinol acetate, salicylic acid, azaleic acid, long chain dicarboxylic acids, sulfur, zinc, various natural agents such as those derived from green tree, and mixtures thereof. Other non-limiting examples of suitable anti-acne actives for use herein are described in U.S. Pat. No. 5,607,980, which description is incorporated herein by reference.

Anti-skin wrinkling actives include a variety of agents, often in combination, that prevent or treat wrinkling through a variety of actions. Many approaches are taken to reduce the appearance of facial wrinkles based on the understanding of the molecular basis of wrinkle formation. Such treatments include cosmetic products, drug therapy and surgical procedures. For example, many cosmetic products contain hydroxy acids, which may stimulate collagen synthesis. Another common treatment utilizes retinol, retinoic, retinol palmitate, a derivative of vitamin A, (or its stronger, prescribed version Retin-A and Renova) which helps collagen production. Bicyclic aromatic compounds with retinoid-type activity, which are useful in particular in preventing or treating various keratinization disorders, are described in EP 679 630. These compounds are particularly active for repairing or combating chronological or actinic ageing of the skin, for example such as in anti-wrinkle products. Antioxidants such as vitamin C and E and coenzyme Q-10 are believed to counteract free radicals, which damage cells and cause aging and have been used in treatments of wrinkles. Recently, the FDA approved cosmetic use of Botox (an extremely diluted form of botulinum toxin) to treat glabella frown lines. Thus non-sunscreen actives of the invention that are anti-skin aging or anti-wrinkling actives may contain, alone or in combination, the bicyclic aromatic compounds defined above, other compounds which have retinoid-type activity, free-radical scavengers, hydroxy or keto acids or derivatives thereof. The term "free-radical scavenger" refers to, for example, α-tocopherol, superoxide dismutase, ubiquinol or certain metal-chelating agents. Hydroxy acids include, e.g., alpha-hydroxy acids such as lactic acid and glycolic acid or beta-hydroxy acids such as salicylic acid and salicylic acid derivatives such as the octanoyl derivative; other hydroxy acids and keto acids include malic, citric, mandelic, tartaric or glyceric acids or the salts, amides or esters thereof.

Other anti-wrinkling agents and anti-skin aging agents useful in the invention include sulfur-containing D and L amino acids and their derivatives and salts, particularly the N-acetyl derivatives, a preferred example of which is N-acetyl-L-cysteine; thiols, e.g. ethane thiol; fat-soluble vitamins, ascorbyl palmitate, ceramides, pseudoceramides (e.g., pseudoceramides described in U.S. Pat. Nos. 5,198, 210; 4,778,823; 4,985,547; 5,175,321, all of which are incorporated by reference herein), phospholipids (e.g., distearoyl lecithin phospholipid), fatty acids, fatty alcohols, cholesterol, plant sterols, phytic acid, lipoic acid; lysophosphatidic acid, and skin peel agents (e.g., phenol and the like), and mixtures thereof. Preferred fatty acids or alcohols are those that have straight or branched alkyl chains containing 12–20 carbon atoms. A particularly preferred fatty acid is linoleic acid since linoleic acid assists in the absorption of ultraviolet light and furthermore is a vital component of the natural skin lipids. Other non-limiting examples of suitable anti-wrinkle actives for use herein are described in U.S. Pat. No. 6,217,888, which description is incorporated herein by reference.

Anti-inflammatory actives include steroidal, non-steroidal, and other compounds.

Non-limiting examples of steroidal anti-inflammatory agents suitable for use herein include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

Nonsteroidal anti-inflammatory agents are also suitable for use herein as skin active agents in the compositions of the invention. Non-limiting examples of non-steroidal anti-inflammatory agents suitable for use herein include oxicams (e.g., piroxicam, isoxicam, tenoxicam, sudoxicam, CP-14, 304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e,g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof. COX-2 inhibitors are also suitable for use herein, and include, but are not limited to, AZD 3582 (ASTRAZENECA and NicOx), Celecoxib (PHARMACIA Corp.) (4-[5-(4-methylphenyl)-3-(trifluoromethyl)-1H-pyrazol-1-yl] benzenesulfonamide), Meloxicam (BOEHRINGER INGELHEIM Pharmaceuticals) (4-hydroxy-2-methyl-N-(5-methyl-2-thiazolyl)-2H-1,2GW-406381 (GLAXOSMITHKLINE), Etoricoxib (MERCK & Co.), Rofecoxib (MERCK & Co.) (4-[4-(methylsulfonyl) phenyl]-3-phenyl-2(5H)-furanone), Lumiracoxib (NOVARTIS Pharma AG), Valdecoxib (PHARMACIA Corp.) (4-(5-methyl-3-phenyl-4-isoxazolyl) benzenesulfonamide), and Etodolac (WYETH Ayerst Laboratories) ((.+-.) 1,8-diethyl-1,3,4,9-tetrahydropyrano-[3,4-b]acid).

Other non-limiting examples of suitable anti-inflammatory or similar other skin active agents include candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, sea whip extract, anise oil, garlic oil, ginger extract, vasoconstrictors such as phenylephrine hydrochloride, and combinations thereof.

Further non-limiting examples of suitable anti-inflammatory or similar other skin active agents include compounds of the Licorice (the plant genus/species Glycyrrhiza glabra) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific non-limiting examples of the foregoing include oil soluble licorice extract, the glycyrrhizic and glycyrrhetic acids themselves, mono ammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, disodium 3-succinyloxy-beta-glycyrrhetinate, and combinations thereof.

Anesthetic actives include butamben picrate, lidocaine, xylocalne, benzocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Analgesic actives include dyclonine hydrochloride, aloe vera, fentanyl, capsaicin, and the like.

Anti-pruritic actives include alclometasone dipropionate, betamethasone valerate, and isopropyl myristate MSD.

Anti-microbial actives include antifungal, antibacterial, and antiseptic compounds. Antifungal compounds include, but are not limited to, compounds such as imidazole antifungals. Specific antifungals include butocouazole nitrate, miconazole, econazole, ketoconazole, oxiconizole, halopro-gin, clotrimazole, and butenafine HCl, naftifine, terbinafine, ciclopirox, and tolnaftate. Antibacterial and antiseptic compounds include phenol-TEA complex, mupirocin, triclosan, chlorocresol, chlorbutol, iodine, clindamycin, CAE (Anjinomoto Co., Inc., containing DL-pyrrolidone Carboxylic acid salt of L-Cocoyl Arginine Ethyl Ester), povidone-iodine, polymyxin b sulfate-bacitracin, zinc-neomycin sulfate-hydrocortisone, chloramphenicol, methylbenzethonium chloride, and erythromycin and antiseptics (e.g., benzalkonium chloride, benzethonium chloride, chlorhexidine gluconate, mafenide acetate, nitrofurazone, nitromersol and the like may be included in compositions of the invention. Many deodorant compounds are also antimicrobial (see below). Antiparasitics, such as lindane may also be included.

Further examples of antimicrobial and antifungal actives useful in the compositions of the present invention include, but are not limited to, β-lactam drugs, quinolone drugs, ciprofloxacin, norfloxacin, tetracycline, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole Compositions of the invention may include antiviral agents. Suitable anti-viral agents include, but are not limited to, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent application Ser. Nos. 09/421,084 (Beerse et al.); 09/421,131 (Biedermann et al.); 09/420,646 (Morgan et al.); and 09/421,179 (Page et al.), which were each filed on Oct. 19, 1999

Anti-allergenics include antihistamines. Antihistamines can be of $H_1$ or $H_2$ antagonists or other types of histamine release inhibitors. The $H_1$ antagonists can be sedating or non-sedating. Examples of $H_1$-sedating antihistamines include diphenhydramine (Benadryl), chlorpheniramine, tripelennamine, promethazine, clemastine, doxylamine, benadryl etc. Examples of $H_1$-non-sedating antihistamines include astemizole, terfenadine, loratadine etc. Examples of $H_2$ antagonists include cimetadine, famotidine, nizatidine, and ranitidine. Examples of histamine-release-inhibitors include cromolyn.

A further active useful in the invention may be a medicinal for treatment of dermatological conditions such as psoriasis, acne, eczema, and other skin conditions due to disease, pathology, accident, and the like. Medicinals include burn relief ointments, such as o-amino-p-toluenesulfonamide monoacetate; dermatitis relief agents, such as the active steroid amcinonide, diflorasone diacetate, and hydrocortisone; diaper rash relief agents, such as methylbenzethonium chloride and the like; herpes treatment drugs, such as O-[(2-hydroxyethoxy)methyl]guanine; psoriasis, seborrhea and scabicide agents, such as shale oil and derivatives thereof, elubiol, ketoconazole, coal tar and petroleum distillates, salicylic acid, zinc pyrithione, selenium sulfide, hydrocortisone, sulfur, menthol, psoralen, pramoxine hydrochloride anthralin, and methoxsalen; steroids, such as 2-(acetyloxy)-9-fluoro-1',2',3',4'-tetrahydro-11-hydroxypregna-1,4-dieno [1 6,17-b]naphthalene-3,20-dione and 21-chloro-9-fluoro-1',2',3',4'-tetrahydro-11 b-hydroxypregna-1,4-dieno[16z, 17-b]naphthalene-3,20-dione, and others including those that are antiinflammatories. Other medicinals include those useful in the treatment of exposure to poison oak, poison ivy, poison sumac, and the like. These include camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, and hydrocortisone acetate. Any other medication capable of topical administration also can be incorporated in a composition of the present invention in an amount sufficient to perform its intended function.

Anticellulite actives include isobutylmethylxanthine, caffeine, theophylline, theobromine, aminophylline, yohimbine, and mixtures thereof.

Examples of actives suitable for treating hair loss include, but are not limited to potassium channel openers or peripheral vasodilators such as minoxidil, diazoxide, and compounds such as N*-cyano-N-(tert-pentyl)-N'-3-pyridinylguanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin EI and prostaglandin F2-alpha; fatty acids, such as oleic acid; diruretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucorcorticoids such as betametasone; botanical extracts such as aloe, clove, ginseng, rehmannia, *swertia*, sweet orange, zanthoxylum, *Serenoa repens* (saw palmetto), *Hypoxis rooperi*, stinging nettle, pumpkin seeds, and rye pollen; other botanical extracts including sandlewood, red beet root, chrysanthemum, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens; verapamil; zidovudine; alpha-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof. Preferred hair loss treatment agents include minoxidil, 6-(I-piperdinyl)-2,4-pyrimidinediamine-3-oxide, N'-cyano-N-(tert-pentyl)-N'-3-pyridinylguanidine, finasteride, retinoids and derivatives thereof, ketoconazole, elubiol or mixtures thereof.

Examples of actives suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone;

amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; impramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof. Preferred hair growth inhibitory agents include serine proteases, retinol, isotretinoin, betamethoisone, alpha-tocophenol and derivatives thereof, or mixtures thereof.

Examples of hair bleaching agents include perborate or persulfate salts.

Deodorant compounds include astringent salts and bioactive compounds. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof. Exemplary aluminum salts include aluminum chloride and the aluminum hydroxyhalides having the general formula $Al_2(OH)_xQ_yXH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconium hydroxy salts, also referred to as zirconyl salts and zirconyl hydroxy salts, and represented by the general empirical formula $ZrO(OH)_2$-nz $L_z$, wherein z varies from about 0.9 to about 2 and is not necessarily an integer; n is the valence of L; 2-nz is greater than or equal to 0; and L is selected from the group consisting of halides, nitrate, sulfamate, sulfate, and mixtures thereof.

Exemplary deodorant compounds therefore include, but are not limited to, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, numerous other useful antiperspirant compounds listed in the CTFA Handbook at p. 56, incorporated herein by reference, and mixtures thereof.

In addition to the astringent salts, the deodorant compound can be a bacteriostatic quaternary ammonium compound, such as, for example, cetyl trimethyl ammonium bromide, cetyl pyridinium chloride, benzethonium chloride, diisobutylbenzoxyethoxyethyldimethylbenzyl ammonium chloride, sodium N-lauryl sarcosine, sodium N-polymethyl sarcosine, lauroyl sarcosine, N-myristolyl glycine, potassium N-lauroyl sarcosine, and stearyl trimethyl ammonium chloride; or a bioactive compound; or a carbonate or bicarbonate salt, such as, for example, the alkali metal carbonates and bicarbonates, and the ammonium and tetralkylammonium carbonates and bicarbonates. Other useful deodorant compounds include chlorophyllin copper complex, aluminum chloride, aluminum chloride hexahydrate, and methylbenzethonium chloride.

Antioxidants are also useful in formulations of the invention. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, tocotrienols and their esters, and 6-hydroxy-2,5,7,8-tetramethylchroman-2-carboxylic acid (commercially available under the tradename TROLOX). Other suitable antioxidants include uric acid and its salts and alkyl esters, sorbic acid and its salts, lipoic acid, amines (e.g., N,N-diethylhydroxylamine, amino-guanidine), sulfhydryl compounds (e.g., glutathione, N-acetyl cysteine), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

Preferred antioxidants are photostable antioxidants. An exemplary photostable antioxidant is marketed under the tradename EMBLICA by EMD Chemicals. See, e.g., U.S. Pat. No. 6,831,191. Antioxidants, preferably photostable antioxidants (e.g., EMBLICA), may be included in sunscreen additives at about 0.05 to about 5%, or about 0.05 to about 2%, or about 0.1%, 0.2%, 0.3%, or 0.4%, or in sunscreen/bodywashes at about 0.02 to about 2%, or about 0.02 to about 1%, or about 0.04%, 0.06%, 0.08%, 0.1%, 0.2%, or 0.3%.

Insect repellants include the most widely used active agent for personal care products, N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into compositions of the invention will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less The compositions of the present invention may contain a wide range of additional active components. The CTFA Cosmetic Ingredient Handbook, Seventh Edition, 1997 and the Eighth Edition, 2000, which are incorporated by reference herein in its entirety, describes a wide variety of active ingredients commonly used in skin care compositions, which are suitable for use in the compositions of the present invention. Other topically-active compounds are listed in Remington's Pharmaceutical Sciences, 20th Ed., Lippincott Williams & Witkins, Baltimore, Md. (2000) (hereinafter Remington's), U.S. Pharmacopeia and National Formulary, The United States Pharmacopeial Convention, Inc., Rockville, Md. and Physician's Desk Reference, Medical Economics Co., Inc., Oradell, N.J. incorporated herein by reference.

The non-sunscreen active may be provided as is or in encapsulated form. Encapsulation is described for sunscreen additives, above. Besides the encapsulated active, in some embodiments an additive or composition for topical application containing the active further includes a cationic polymer, as described herein, as well as, optionally, a film former, a preservative, and/or an antioxidant that is stable upon exposure to sunlight. Other components may be as described herein. In some embodiments the additive or composition for topical application may comprise two, three, four, five, six, seven, eight, nine, ten, or more than ten actives, each of which may be encapsulated or non-encapsulated, in any combination.

In preferred embodiments, the active is encapsulated sol-gel microcapsules, such as silica sol-gel microcapsules. Such microcapsules are described in U.S. Pat. Nos. 6,238,650; 6,436,375, 6,303,149; and 6,468,509. Thus, in some embodiments the invention provides an additive for addition to a composition for topical application, where the additive comprises an encapsulated non-sunscreen active, and optionally further comprises a cationic polymer. In other embodiments the invention provides a composition for topical application that contains an additive, where the additive comprises an encapsulated non-sunscreen active, and optionally further comprises a cationic polymer. Further ingredients include film formers, antioxidants, preservatives, and other ingredients as listed herein. The composition for topical application may be, e.g., a bodywash.

In some embodiments the invention provides microcapsules, e.g., sol-gel microcapsules (e.g., as described in U.S. Pat. Nos. 6,238,650; 6,436,375, 6,303,149; and 6,468,509) that act as a protective barrier on the skin when used either alone, or as an additive in a bodywash. In these embodiments, the sol-gel microcapsules may be used without any additional active ingredients (i.e., empty), providing a physical barrier, or they may be used with additional encapsulated active ingredients that enhance their barrier function. For example, the microcapsules may contain substances that act to screen toxic agents (e.g., biological or chemical warfare agents) or radiation (e.g., alpha, beta, or gamma radiation) partially or completely from penetrating the user's skin. In some embodiments, the microcapsules may contain one or more agents that absorb radiation, such as graphite, lead, tungsten, and others known in the art, or agents that reflect radiation such as ceramic beads. As the microcapsules may be designed so as to experience minimal or no breakage when applied to the skin, as well as to experience minimal penetration of the skin, it is possible to use even toxic substances (e.g., lead) that provide a screening effect, since these substances will not be released or will be released in only minimal amounts. The microcapsules are eventually removed from the skin through repeated washing and/or normal sloughing of the external skin cell layers. Especially for agents used for one-time or very few exposures, such as can occur for personnel engaged in combating or containing terrorist attacks or in warfare, the invention provides a means to deliver a last line of defense on the skin of personnel where the active used in the microcapsules may be one that is not appropriate for long-term use, but that is appropriate for a limited number of applications in order to protect the wearer from a greater risk (e.g., microcapsules encapsulating lead to protect against a radiation attack).

The microcapsules, e.g., sol-gel microcapsules, can be prepared so as to experience no or minimal breakage when applied to the skin, either as is or in the form of a bodywash. Alternatively, the microcapsules, e.g., sol-gel microcapsules, can be prepared so as to experience various degrees of breakage, on average, when applied as is or in a bodywash. Thus, the microcapsules, e.g., sol-gel microcapsules, may be prepared so as to experience about 0% breakage, or breakage in a range from about 0.1, 0.5, 1, 2, 5, 10, 20, 30, 40, 50, 60, 70, 80, or 90% to about 0.5, 1, 2, 5, 10, 20, 30, 40, 50, 60, 70, 80, or 90%, after application (or application and rinsing in the case of a bodywash containing the microcapsules). Furthermore, the microcapsules may be formulated so as to break open in response to conditions that occur on the skin, so that after application the microcapsules act to release their contents in a time-release or controlled manner. Non-limiting exemplary skin or hair conditions that can vary with the user's environment, the variation of which can trigger breakage of microcapsules, include pH, temperature, friction, exposure to light or air, pressure, and the like.

C. Cationic Component

In some embodiments the additives, e.g., sunscreen additives and sunscreen/bodywashes of the invention further include a cationic component. Without being bound by theory, it is thought that this component serves as a protein binder, to provide a positive charge to promote attachment of the composition to proteins of the skin and hair, thus increasing retention of the components, e.g., sunscreen, after rinse and during normal activities. This positive charge creates a strong affinity for the protein in the hair or skin. Any means of imparting a positive charge may be used.

Preferred means are by including one or more cationic polymers in the composition. Various cationic polymers may be used. Examples of cationic polymers are described in U.S. Pat. Nos. 6,224,852; 3,816,616; 4,272,515; 4,298,494; 4,080,310; 4,048,301; 4,009,256; and 3,186,911. Cationic polymers are available commercially, e.g., from Union Carbide Corp. under the trademark POLYMER JR., from Celanese-Stein Hall under the trademark JAGUAR, from GAF Corporation under the tradename Gafquatm and from Merck & Co., Inc under the trademark MERQUAT by. Representative one are Merquat 100, a highly charged cationic dimethyldiallylammonium chloride homopolymer, and Merquat™ 550, a highly charged cationic copolymer prepared with dimethyldiallylammonium chloride and acrylamide. These materials are designated in the CTFA dictionary as Quaternium40 and Quaternium-41, respectively.

Especially preferred are polyquaterniums. Quaternized material in powder form, not limited to the polyquaterniums, may also be used. Exemplary polyquaterniums of use in the invention include polyquaternium-4, -7, -11, -22, -37, -44, -5, and -64. Polyquaternium compounds are available commercially, e.g., CELQUAT L-200 for polyquaternium-4. Without being limited by theory, it is thought that with the trapping of the encapsulate (e.g., sunscreen active inside the capsule) by this cationic component. rinse off is difficult and renders the active substantive to the protein in the skin and hair.

Useful in some embodiments of the invention is a dry cationic component, such as sold under the tradename CAE (Anjinomoto Co., Inc.), containing DL-pyrrolidone Carboxylic acid salt of L-Cocoyl Arginine Ethyl Ester, which is a cationic agent useful for binding to proteins and providing an antimicrobial effect.

In some embodiments of additives, e.g., sunscreen additives, the cationic component (e.g., cationic polymer) comprises about 0.1 to about 20%, or about 0.1 to about 10%, or about 0.5 to about 10%, or about 1 to about 10%, or about 0.5 to about 5%, or about 0.5 to about 3% or about 1 to about 5%, or about 1 to about 3%, or about 1% of the total composition. In some embodiments, the cationic component is polyquaternium-4; in some embodiments the polyquaternium-4 is present at about 1%.

In some embodiments of active/bodywashes, e.g., sunscreen/bodywashes, the cationic component (e.g., cationic polymer) comprises about 0.03 to about 7%, or about 0.03 to about 4%, or about 0.2 to about 4%, or about 0.3 to about 4%, or about 0.2 to about 2%, or about 0.3 to about 4%, or about 0.3 to about 1%, or about 0.3 or 0.4% of the total composition. In some embodiments, the cationic component is polyquaternium-4; in some embodiments the polyquaternium-4 is present at about 0.33%.

D. Film Formers

In some embodiments, compositions of the invention further include a component that provide a film barrier system, typically a hydrophobic layer that serves to maintain the residual sunscreen after rinse. Film barrier systems are well-known in the art and include, without limitation, petrolatum, silicon derivatives, and combinations thereof. Also useful are polymers with carboxylic ends which render themselves insoluble until neutralized. After being neutralized they can act as film formers. Film formers also include emollient esters, lanolin derivatives (e.g., acetylated lanolins), and superfatted oils. Film formers are available commercially, e.g., a preferred film former is MOISTURE-GUARD™, which contains petrolatum, dimethicone, stearamidopropyl dimethylamine stearate, and tocopheryl acetate, available from Engelhard.

It may also be desirable to add acrylic co-polymers to the formulations of the invention as film formers. An exemplary liquid acrylic copolymer formulation is DERMACRYL, marketed by National Starch and Chemical. Acrylic co-polymers may be included in sunscreen additives at about 0.1 to about 5%, or about 0.2 to about 3%, or about 0.2%, 0.3%, 0.4%, or 0.5%, or in sunscreen/bodywashes at about 0.05 to about 2%, or about 0.1 to about 1%, or about 0.05%, 0.1%, 0.2%, 0.3%, 0.4%, or 0.5%.

A secondary film former may also be used, e.g., keratin or other protein derivative in an amino acid complex such as cysteine.

The film former may be present in the sunscreen additive in the range of about 0.1 to about 25%, or about 1 to about 10%; or about 2 to about 6%; or about 3, 4, or 5%. In some embodiments, the film former MoistureGuard is used at a concentration of about 4.2%. Equivalent film formers, at equivalent concentrations, may also be used.

As noted, some preparations may perform more than one function, for example, inorganic blockers such as Tioveil and Spectraveil (both of the Tioxide Group), in certain variations, may be film-formers and may have advantageous uses here.

In addition, many emollients may also perform a film former function in that they provide a barrier on the skin. Thus, compositions of the invention may include water-insoluble emollients that include fatty acids such as oleic and stearic; fatty alcohols such as cetyl, and hexadecyl (ENJAY); esters such as diisopropyl adipate, benzoic acid esters of $C_9$–$C_{15}$ alcohols, and isononyl iso-nonanoate; alkanes such as mineral oil; silicones; such as dimethyl polysiloxane and ethers such as polyoxypropylene butyl ethers and polyoxypropylene cetyl ethers. If a water-insoluble emollient is used it may be in an amount from about 2% to about 15% by weight, and most preferably from about 4% to about 10%.

Other useful film formers include polythylenes, such as those available from New Phase Technologies as PERFOR-MALENE 400, a polyethylene having a molecular weight of 400. Another suitable water-proofing agent is polyethylene 2000 (molecular weight of 2000), which is available from New Phase Technologies as PERFORMALENE 2000.

Yet another suitable film former/waterproofing agent is synthetic wax, also available from New Phase Technologies as PERFORMA V-825. Still yet another suitable film former/waterproofing agent is octadecene/MA copolymer Additional film formers which also may be used within the framework of the invention include any film former chemistry known in the art. Thus, suitable additional film formers include acacia gum, cellulose derivatives, guar derivatives and all those set forth on pages 68–69 of the C.T.F.A. Cosmetic Ingredient Handbook, First Edition, 1988, which is hereby incorporated by reference. Such film formers include acrylamides copolymer, acrylamide/sodium aciylate copolymer, acrylate/acrylamide copolymer, acrylate/ammonium methacrylate copolymer, acrylates copolymer, acrylates/diacetoneacrylamide copolymer, acrylic/acrylate copolymer, adipic acid/dimethylaminohydroxypropyl diethlenetnamine copolymer, adipic acid/epoxypropyl/diethlenetriamine copolymer, albumen, allyl stearate/VA copolymer, aminoethylacrylate phosphate/acrylate copolymer, ammonium acrylates copolymer, ammonium alginate, ammonium vinyl acetate/acrylates copolymer, AMP acrylates/diacetoneacrylamide copolymer, balsam canada, balsam oregon, balsam peru, balsam tolu, benzoi acid/phthalic anhydride/pentaerythritol/neopentyl glycol/palmitic acid copolymer, benzoin extract, butadiene/acrylonitrile copolymer, butylated urea-formaldehyde resin, butyl benzoic acid/phthalic anhydride trimethylolethane copolymer, butyl ester of ethylene maleic anhydride copolymer, butyl ester of PVM/MA copolymer, calcium carrageenean, calcium/sodium PVM/MA copolymer, carboxymethyl hydroxyethyl cellulose, cellulose gum, collodion, copal, corn starch/aciylainide/sodium acrylate copolymer, damar, diethylene glycolamine/epichlorohydrin/piperazine copolymer, DMJ-IF, dodecanedoic acid/cetearyl alcoholglycol copolymer, ethylcellulose, ethylene/acrylate copolymer, ethylene/maleic anhydride copolymer, ethylene/vinyl acetate copolymer, ethyl ester of PVM/fvIA copolymer, flexible collodian, gum benzoin, gutta percha, hydroxybutyl methylceflulose, hydroxyethylcellulose, hydroxyethyl ethyl cellulose, hydroxypropylceilulose, hydroxypropyl guar, hydroxypropyl methylcellulose, isopropyl ester of PVM/MA copolymer, maltodextrin, melamine/formaldehyde resin, methacryloyl ethyl betainelmethacrylates copolymer, nitrocellulose, octylacrylamide/acrylates/butylaminoethyl-methaciylate copolymer, octylacrylamide/acrylates copolymer, phthalic anhydride/glycerin/gycidyl decanoate copolymer, phthalic/trimellitic/glycols copolymer, polyacrylamide, polyaciylamidomethylpropane sulfone acid, polyacrylic acid, polybutylene terephthalate, polychlorotrifluoroethylene, polyethylacrylate, polyethylene, polyethylene terephthalate, polyisobutene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, polystyrene, polyvinyl acetate, polyvinyl alcohol, polyvinyl butyral, polyvinyl imidazolinium acetate, polyvinyl laurate, polyvinyl methyl ether, potassium carrageenan, PVM/MA copolymer, PVP, PVP/dimethylaminoethymethacrylate copolymer, PVP/eicosene copolymer, PVP/ethyl methacrylate/methacrylic acid copolyerm, PVP/hexadecene copolymer, PVP/VA copolymer, PVP/vinyl acetate/itaconic acid copolymer, rosin, serum albumin, shellac, sodium acrylate/vinyl alcohol, copolymer, sodium carrageen, sodium polymethacrylate, sodium polystyrene sulfonate, starch/acrylates/acrylamide copolymer, starch diethylaminoethyl ether, steaxyvinyl ether/maleic anhydride copolymer, styrene/acrylate/acrylonitrile copolymer, styrene/acrylate/ammonium methacrylate copolymer, styrene/maleic anhydride copolymer, styrene/PVP copolymer, sucrose benzoate/sucrose acetate isobutyrate/butyl benzyl phthalate copolymer, sucrose benzoate/sucrose acetate isobutyrate/butyl benzyl phthalate/methyl methaciylate copolymer, sucrose benzoate/sucrose acetate isobutyrate copolymer, toluenesulfonamide/formaldehyde resin, tragacath gum, vinyl acetate/crotonates copolymer, vinyl acetate/crotonic acid copolymer, vinyl acetate/crotonic acid/methacryloxybenzophenon-1 copolymer, vinyl acetate/crotonic aid/vinyl neodecanoate copolymer, and zein Additional film formers include those set forth in U.S. Pat. Nos. 6,838,419; 6,838,088; 6,780,422; 6,531,118; and 5,916,541, all of which are incorporated herein by reference E. Other Components A wide variety of additional components may be added to the compositions of the present invention, as long as the components are selected so as to avoid any undesirable reaction with the primary components (e.g., one or more of the sunscreen agents) of the composition. The CTFA Cosmetic Ingredient Handbook, Seventh Edition, 1997 and the Eighth Edition, 2000 (incorporated by reference herein), provide a broad source of possible cosmetic and pharmaceutical ingredients typically used in skin care compositions. Examples of such additional components include one or more of the following: Absorbents, abrasives, anticaking agents, antifoaming agents, binders, biological additives, buffering agents, bulking agents, chelating agents/sequestrants (e.g., disodium EDTA), chemical additives, colorants, cosmetic astringents, cosmetic biocides, denaturants, drug astringents, emollients (including glycerin alovera, and Vitamins A, C, and D [hydrating agents and skin protectants]), foam boosters, fragrance components, gums, humectants/moisturizers (including urea, guanidine, glycolic acid, polyhydroxy alcohols such as sorbitol, glycerin, hexanetriol, propylene glycol, hexylene glycol and the like, polyethylene glycol, sugars and starches, sugar and starch derivatives, D-panthenol, hyaluronic acid, lactamide monoethanolamine, acetamide monoethanolamine, and mixtures thereof), hydrotropes, neutralizing agents, opacifying agents and pigments, pH adjusters, plasticizers, preservatives, propellants, reducing agents, skin bleaching agents, skin protectants, solubilizing agents, and suspending agents (e.g., Carbomer 1382).

In some embodiments, the additives and bodywashes of the invention, e.g., sunscreen additives or sunscreen/bodywashes include a preservative. Exemplary preservatives useful in the invention include citric acid, tartaric acid, phosphoric acid, iminodiacetic acid, nitrilotriacetic acid, hydroxyethyleneaminodiacetic acid and ethylenediaminetetraacetic acid and salts thereof; para-hydroxybenzoates such as butyl paraben, methyl paraben and propyl paraben; imidazolines (e.g., imidiazolinylurea), triclosan, hydantoins (e.g., dimethyloldimethylhydantoin), isothiazolidinone compounds and mixtures thereof. Commercially available preservatives include KATHON CG and KATHON CGII, which contain methylchloroisothiazolinone and methylisothiazolinone (Rohm and Haas). When present, the quantity of preservative is in the range from 0.001 to 2%, preferably from 0.01 to 0.2%.

In certain embodiments the compositions of the invention include a chelating agent. Chelating agents are substances used to chelate or bind metallic ions, such as with a heterocyclic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the additives or additive/bodywashes in amounts ranging from about 0.001 to about 0.2 weight percent, or about 0.01% weight percent.

Thickening agents or gellants may be added as desired to adjust the texture and viscosity of the composition. Exemplary agents or gellants may be selected from Carbopol™ resins [e.g., 934, 971, 974, 980, 981] and Pemulen™ [TR-1 and TR-2] [both Carbopol™ and Pemulen™ are registered trademarks of BF Goodrich], Noveon AA-1, ETD resins, and Ultrez™ resins [registered trademark, BF Goodrich]. In addition, carbomers might be useful for this purpose.

It may be desired to include a non-polar wax. Examples of such useful waxes include ester waxes, diester waxes, hydrocarbon waxes, silicone waxes and triglyceride waxes and mixtures thereof.

Other components may include a liquid hydrocarbon (similar to pentane), and/or a cationic foaming agent derived from arginine and or cysteine.

Further optional ingredients which can be present in the composition include fragrance, dyes, antimicrobial materials such as triclocarban, triclosan, iodophors, iodine formulations, phenolic compounds, e.g. hexachlorophene, and bisbiguanides, e.g. chlorhexidene gluconate, and the like. See, e.g., U.S. Pat. Nos. 6,827,795; 6,517,854; 6,010,817; 5,173,216; 5,719,113; 5,259,984; 5,562,912; 5,629,006; 5,728,662; 5,767,163; 5,750,579; 5,591,442; 5,650,143; 5,772,640; and 4,478,821.

The components of the composition are generally mixed in water.

F. Surfactants and Bodywashes

Compositions of the invention may be formulated as products for washing the skin, for example, bath or shower gels, hand washing compositions or facial washing liquids; pre- and post-shaving products; rinse-off, wipe-off and leave-on skin care products; products for washing the hair and for dental use. Shower gels are particularly preferred product forms.

If it is desired to prepare a sunscreen/bodywash composition, the sunscreen additives of the invention may be combined with other ingredients to produce a bodywash (e.g., a liquid or solid formulation). The sunscreen/bodywash may include one or more surfactants. The use of surfactants in bodywashes is well-known in the art. Any surfactant known in the art and appropriate for a bodywash composition may be used. See, McCutcheon's *Detergents & Emulsifiers*, M.C. Publishing Co. (North American edition 1989); Schwartz, et al., *Surface Active Agents, Their Chemistry and Technology*, New York, Interscience Publishers, 1949, and U.S. Pat. Nos. 6,096,697; 4,741,855; 4,788,066; 5,104,646; 5,106,609; 2,658,072; 2,438,091; 2,528,378; 2,486,921; 2,486,922; 2,396,278; 2,979,465; 3,179,599; 5,322,643; 5,084,212; 3,332,880; 4,122,029; 4,265,878; 4,421,769; 3,929,678; 3,959,461; 4,387,090; 4,303,543; and 6,224,852; and in British Patent Nos. 848,224 and 791,415. Also see CTFA Cosmetic Ingredient Dictionary, $4^{th}$ Edition 1991, pages 509–514 for various long chain alkyl cationic surfactants; and Richmond, James M., *Cationic Surfactants*, Marcel Dekker, Inc., New York and Basel, 1990.

The surfactant(s) may be cationic, anionic, nonionic, zwitterionic, amphoteric, or any combination thereof.

Specific examples of anionic surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention. Specific examples of alkyl sulfates that may be used are sodium, ammonium, potassium, magnesium, or TEA salts of lauryl or myristyl sulfate. Examples of alkyl ether sulfates that may be used include ammonium, sodium, magnesium, or TEA laureth-3 sulfate.

Another suitable class of anionic surfactants are the sulfated monoglycerides of the form R1CO—O—CH$_2$—C(OH)H—CH$_2$—O—SO$_3$M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. An example of a sulfated monoglyceride is sodium cocomonoglyceride sulfate.

Other suitable anionic surfactants include olefin sulfonates of the form R1SO$_3$M, wherein R1 is a mono-olefin having from about 12 to about 24 carbon atoms, and M is a water-soluble cation such as ammonium, sodium, potassium, magnesium, triethanolamine, diethanolamine and monoethanolamine. An example of a sulfonated olefin is sodium C14/C16 alpha olefin sulfonate.

Other suitable anionic surfactants are the linear alkylbenzene sulfonates of the form R$_1$—C$_6$H$_4$—SO$_3$M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. An example of this anionic surfactant is sodium dodecylbenzene sulfonate.

Still other anionic surfactants suitable for the compositions of the present invention include the primary or secondary alkane sulfonates of the form R1 SO$_3$M, wherein R1 is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. An example of an alkane sulfonate useful herein is alkali metal or ammonium C 13–C 17 paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates that are based on taurine. Examples of taurates include N-alkyltaurines such as the one prepared by reacting dodecylamine with sodium isethionate as detailed in U.S. Pat. No. 2,658,072.

Another class of suitable anionic surfactants is the acyl isethionates. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form R1—OCH$_2$—C(OH)H—CH$_2$—SO$_3$M, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. One example is sodium cocoglyceryl ether sulfonate.

Other suitable anionic surfactants include: Sulfonated fatty acids of the form R1-CH(SO$_4$)—COOH and sulfonated methyl esters of the from R1-CH(SO$_4$)—CO—O—CH$_3$, where R1 is a saturated or unsaturated, branched or unbranched alkyl group from about 8 to about 24 carbon atoms (e.g., alpha sulphonated coconut fatty acid and lauryl methyl ester); phosphates such as monoalkyl, dialkyl, and trialkylphosphate salts formed by the reaction of phosphorous pentoxide with monohydric branched or unbranched alcohols having from about 8 to about 24 carbon atoms (e.g., sodium mono or dilaurylphosphate, ethoxylated monoalkyl phosphates, etc.); acyl glutamates corresponding to the formula R1CO—N(COOH)—CH$_2$CH$_2$—CO$_2$M wherein R1 is a saturated or unsaturated, branched or unbranched alkyl or alkenyl group of about 8 to about 24 carbon atoms, and M is a water-soluble cation (e.g., sodium lauryl glutamate and sodium cocoyl glutamate); alkanoyl sarcosinates corresponding to the formula R1CON(CH$_3$)—CH$_2$CH$_2$—CO$_2$M wherein R1 is a saturated or unsaturated, branched or unbranched alkyl or alkenyl group of about 10 to about 20 carbon atoms, and M is a water-soluble cation (e.g., sodium lauroyl sarcosinate, sodium cocoyl sarcosinate, and ammonium lauroyl sarcosinate); alkyl ether carboxylates corresponding to the formula R1—(OCH$_2$CH$_2$)x—OCH$_2$—CO$_2$M wherein R1 is a saturated or unsaturated, branched or unbranched alkyl or alkenyl group of about 8 to about 24 carbon atoms, x is 1 to 10, and M is a water-soluble cation (e.g., sodium laureth carboxylate); acyl lactylates corresponding to the formula R1CO—[O—CH(CH$_3$)—CO]x—CO$_2$M wherein R1 is a saturated or unsaturated, branched or unbranched alkyl or alkenyl group of about 8 to about 24 carbon atoms, x is 3, and M is a water-soluble cation (e.g., sodium cocoyl lactylate); carboxylates, nonlimiting examples of which include sodium lauroyl carboxylate, sodium cocoyl carboxylate, and ammonium lauroyl carboxylate; anionic flourosurfactants; and natural soaps derived from the saponification of vegetable and/or animal fats & oils examples of which include sodium laurate, sodium myristate, palmitate, stearate, tallowate, cocoate.

Any counter cation, M, can be used on the anionic surfactant. Preferably, the counter cation is selected from the group consisting of sodium, potassium, ammonium, monoethanolamine, diethanolamine, and triethanolamine.

Nonlimiting examples of nonionic surfactants that may be included in the compositions of the present invention include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g., C8–30 alcohols, with sugars or starches or sugar or starch polymers, i.e., glycosides or polyglycosides. These compounds can be represented by the formula (S)$_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides Processes for making compositions containing polyhydroxy fatty acid amides are disclosed, for example, in G.B. Pat. Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934.

Other examples of nonionic surfactants include amine oxides. Amine oxides correspond to the general formula $R_1R_2, R_3N \rightarrow O$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH.sub.2).sub.3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Examples of amphoteric surfactants of the present invention include the following compounds: Cetyl dimethyl betaine (this material also has the CTFA designation cetyl betaine); Cocamidopropylbetaine; Cocamidopropyl hydroxy sultaine. Examples of other useful amphoteric surfactants are alkyliminoacetates, and iminodialkanoates and aminoalkanoates of the formulas $RN[(CH_2) CO_2 M]_2$ and $RNH(CH_2)._mCO_2 M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091; and the products sold under the trade name "Miranol" and described in U.S. Pat. No. 2,528,378. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

In preferred embodiments, the sunscreen/bodywashes of the invention include at least one cationic surfactant. Many cationic surfactants are known to the art. Suitable cationic surfactants include, but are not limited to, fatty amines, di-fatty quaternary amines, tri-fatty quaternary amines, imidazolinium quaternary amines, and combinations thereof. Suitable fatty amines include monalkyl quaternary amines such as cetyltrimethylammonium bromide. A suitable quaternary amine is dialklamidoethyl hydroxyethylmonium methosulfate. By way of example, the following may be mentioned: stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated)dimethyl ammonium chloride; dilauryldimethyl ammonium chloride; and stearalkonium chloride. Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by reference.

The total surfactants, e.g., cationic surfactant, may be present in the sunscreen/bodywash at about 0.1 to about 20%, or about 0.1 to about 10%, or about 0.1 to about 5%, or about 0.5 to about 5%, or about 1 to about 10%, or about 1 to about 5%, or about 0.1 to about 2%, or about 1 to about 2%. In some embodiments, a sunscreen/bodywash composition of the invention contains a surfactant, e.g., a cationic surfactant, at about 1%.

In addition to surfactants, other ingredients, as described above for additives, may be included in the additive/bodywash. Any component known in the art or useful in bodywashes may be used.

In some embodiments, soapless cleansers may be used in addition to, or instead of, soaps/surfactants. For example, Oilatum™ AD (registered trademark, Stiefel Laboratories), Aquanil™ (registered trademark, Person & Covey, Inc.), Cetaphil™ (trademark, Galderma Laboratories, Inc.) or SpectroDerm™ (registered trademark, Draxis Pharmaceutical Inc.), or their equivalents, may be utilized as a soapless component in the present invention.

As noted above, the sunscreen additives of the invention may also be combined with conventional bodywash compositions, as well as with shampoos for hair, and post-wash skincare compositions. Proportions for addition and mixing are given above as well as in more detail hereafter. An exemplary bodywash that may be used with additives of the invention is exemplified by SUAVE Body Wash. Ingredients of a typical SUAVE bodywash include: Water, Ammonium Lauryl Sulfate, Ammonium Laureth Sulfate, Cocamidopropyl Betaine, Fragrance, Glycerin, Hydrolyzed Milk Protein & Honey Extract, PEG-10 Sunflower Glycerides, Cocamide MEA, Guar Hydroxypropylrimonium Chloride, Acrylates Copolymer, PEG-5 Cocamide, *Helianthus Annuus* (Sunflower) Seed Oil or Glycine Soja (Soybean) Oil, Tetrasodium EDTA, Propylene Glycol, Ammonium Chloride, Sodium Hydroxide, Methylchloroisothiazolinone, Methylisothiazolinone, Titanium Dioxide (CI 77891)

II. Methods

A. Preparation

The compositions of the invention may be prepared by any suitable method. In one preferred method, a "Phase I," which is a "water phase," is prepared by mixing the more water-soluble components of the composition. For example, Polyquaternium-4, a film former (e.g., in MOISTURE-GUARD), and encapsulated sunscreen (e.g., in UV PEARLS), may be mixed until uniform. A "Phase II," which is an "oil phase," is prepared by mixing the more hydrophobic components of the composition. For example, Avobenzone (e.g., PARSOL 1789) may be mixed with Octocrylene, with heating, until dissolved. Then Phase I and Phase II are combined with gentle agitation, until a uniform composition is obtained (Phase III). Phase III may be further combined with a bodywash composition (e.g., SUAVE bodywash) and mixed until uniform. A further sunscreen, such as titanium dioxide, may be added to the Phase III/bodywash composition and mixed until uniform. Alternatively, the sunscreen may be added before addition to the bodywash or soap to provide an additive ready for formulation with a bodywash or soap.

B. Use

Additives, e.g., sunscreen additives of the invention are generally designed to be used in combination with a bodywash. Thus, the compositions of the invention are typically designed to be applied while washing. This characteristic facilitates ease of use and may have the added benefit of being cumulative. Compositions of the present invention are readily applied during washing in a suitable or effective amount and may be generally applied all over the body. Shampoos may be applied specifically to the hair. A selected amount of a composition may be applied directly to the skin or may be used through intermediate application to a washcloth, pad, sponge, or other applicator. After lathering, dirt and sloughed-off skin may be washed away by rinsing with water leaving behind one or more of the additives, e.g., sunscreen components. Additives of the invention, e.g., sunscreen additives of the invention are also useful in hair shampoos and conditioners, and in after-wash lotions.

Thus, methods of the invention include methods for protection of skin from sunlight, comprising applying a bodywash comprising a sunscreen to the skin, wherein after application of the bodywash to skin and rinsing, the skin is protected from sunlight with an average SPF of at least about 2, 3, 4, 5, 6, 7, 8, 9, 10, 11, 12, 1.3, 14, 15, 16, 17, 18, 19, 20, or more than 20. In some preferred embodiments, the skin is protected from sunlight with an average SPF of at least about 2. In some preferred embodiments, the skin is protected from sunlight with an average SPF of at least about 5. In some preferred embodiments, the skin is protected from sunlight with an average SPF of at least about 10. In some preferred embodiments, the skin is protected from sunlight with an average SPF of at least about 15. In some embodiments, the bodywash is applied more than once; in these cases, the SPF may be cumulative and can increase with the second wash to, e.g., an average of more than 2, 5, 6, 7, 8, 9, 10, 11, 12, 13, 15, 15, 16, 17, 18, 19, 20, 21, 22, 23, 24, 25, 30, 35, 40, 45, or more than about 45. In some embodiments the bodywash is applied once per day. In some embodiments, the bodywash is applied more than once per day, for example, 2, 3, 4, or more than 4 times per day. In some embodiments, the bodywash is applied about every other day. In some embodiments, the body wash is applied about 10, 8, 7, 6, 5, 4, 3, 2 or 1 time per week.

In these methods, the active additive, e.g., sunscreen, often does not penetrate beyond a certain level in the skin, typically due to encapsulation. Thus, in some embodiments of the methods of the invention, the active additive, e.g., sunscreen, does not penetrate more than about 10, 20, 25, 30, 35, 40, 45, or 50 microns into the skin with one washing with a bodywash containing the additive. In some embodiments, the active additive, e.g., sunscreen, does not penetrate more than about 10, 20, 25, 30, 35, 40, 45, 50, 60, 70, 80, 90, 100, 120, or 150 microns into the skin, even with repeated washings.

In other embodiments the sunscreen or other additive is designed to penetrate into the skin, thus, in these embodiments, the active additive, e.g., sunscreen, penetrates to at least about 10, 20, 25, 30, 35, 40, 45, or 50 microns into the skin with one washing with a bodywash containing the additive. In some embodiments, the active additive, e.g., sunscreen, penetrates more than about 10, 20, 25, 30, 35, 40, 45, 50, 60, 70, 80, 90, 100, 120, or 150 microns into the skin. In some embodiments this penetration occurs with a single washing and rinsing. In some embodiments this penetration occurs with repeated washings and rinsings.

Any additive described herein, e.g., sunscreen additives, generally as a component of a bodywash, may be used in the methods of the invention. In some embodiments, the additive is a non-sunscreen additive and is encapsulated, e.g., in the form of sol-gel microcapsules. In these embodiments, the additive may be used in combination with a non-bodywash vehicle, such as a skin lotion, gel, cream, and the like, as are well-known in the art.

While it is ordinarily preferred to use the compositions of the present invention in a manner similar to ordinary soap (i.e., wetting, application of composition, rinsing), it is also anticipated that the composition may be used by application without wetting followed by removal through, for example, wiping. This is the case for soapless cleansers.

C. Business Methods

The invention also encompasses methods of doing business in the field of topical delivery of cosmeceuticals and the transdermal delivery of pharmaceuticals using lathering products, including everyday soap and shampoo, as the delivery agents.

Consumers spend more than $30 billion annually on products that take advantage of topical and transdermal delivery methods. Despite enormous growth in this area, there have been few major innovations. Most delivery methods still rely on lotions, creams or patches. By combining a cosmetic or even pharmaceutical regimen with an activity as routine as washing up or showering, the business methods of the invention capture a significant share of the topical and transdermal delivery market. Products enable personal care product makers to secure a piece of the growing market for cosmeceuticals, like sunscreen, by enhancing existing product lines. They will also enable drug makers to offer consumers more appealing ways to administer prescription and over-the-counter pharmaceuticals Business methods of the invention encompass a method of doing business comprising marketing an additive for use with an existing bodywash, wherein the additive, when combined with the bodywash, causes an additional effect to the normal effect of the soap or the bodywash. The business methods include methods involving any of the additives described herein, including sunscreens, insect repellants, anti-acne medications, anti-wrinkling agents, deodorants, and all others described herein In some embodiments, the methods include marketing a sunscreen benefit agent (additive) for use with a bodywash, e.g., bar and liquid soaps, and shampoos, to add the benefit of a sunscreen. The sunscreen may be any one of the sunscreen additives described herein. This embodiment is designed to appeal to soap manufacturers looking to broaden the market for their products among the growing population of consumers concerned about skin cancer and wrinkles. Generally, the benefit agent is marketed as a brand-neutral additive for use with existing brands. In some cases, a stand-alone brand may be created.

The sunscreen or other benefit agent may be licensed as an additive, in both liquid and bar soap forms, to personal care product makers of all sizes, to enhance and differentiate their branded product offerings. The license may be exclusive or, preferably, non-exclusive. If exclusive, it may be exclusive in a defined geographical territory, for a defined time period (often with an option to renew or right of first refusal at the expiration of the time period), for a defined type of skin care product, or any combination of these. The methods also include supplying one or more customers with an option to license or buy the additive, generally for a defined period of time. As with licenses, such an option may be exclusive or non-exclusive. Alternatively, the sunscreen or other benefit agent may be manufactured and supplied to personal care product makers. A further alternative is to manufacture a stand-alone brand of soap/bodywash that includes the additive.

A further component of the business methods of the invention typically includes receiving payment for supplying the additive, license, or the like, to the customer. It will be appreciated that "payment" may be any form of consideration, included monetary consideration. Typically, license payments take the form of an up-front payment, royalties, license maintenance fees or some combination thereof. Also included in payment options are equity in the company receiving the additive or the license to the additive. It will be appreciated that any other form of consideration may also constitute payment in the business methods of the invention The business methods of the invention may further include manufacturing the additive and/or the additive/bodywash. In some embodiments, different entities perform different aspects; for example, a first entity may manufacture the additive and a second entity may market and/or distribute it. In some embodiments, a single entity performs both manufacturing and marketing.

Business methods of the invention further include a method including the steps of: a) designing an additive for use in a personal care product; b) testing the additive for safety and effectiveness in humans; c) arranging for distribution and marketing of the additive. In some embodiments, steps a) and c) are performed by a first entity, typically a business entity, and step b) is performed by a second entity, such as a business entity or an academic entity. In some or these embodiments, step b) is performed as a joint venture between the two entities.

All publications and patent applications mentioned in this specification are herein incorporated by reference to the same extent as if each individual publication or patent application was specifically and individually indicated to be incorporated by reference.

It will be apparent to one of ordinary skill in the art that many changes and modification can be made to the disclosures presented herein without departing from the spirit or scope of the appended claims.

EXAMPLES

Example 1

A sunscreen additive for addition to a bodywash was prepared as follows: To 13.7 g water was added 1 g of polyquaternium-4 (CELQUAT-200), 1.5 gm of MOISTUREGUARD, and 12 g of UV PEARLS. The mixture was stirred until uniform, to produce Phase I. Separately, 1 g of PARSOL 1789 was added to 4 g of Octocrylene with heating, and stirred until uniform, to produce Phase II. Phase I and Phase II were combined with gentle agitation until uniform to produce Phase III, a sunscreen additive.

The sunscreen additive of Phase III was added to 64.5 g of SUAVE Bodywash and stirred until uniform. Finally, 2.3 g of titanium dioxide were added with stirring. The final composition was a sunscreen/bodywash.

Example 2

The sunscreen/bodywash of Example 1 was tested for SPF capability as follows: 50 $cm^2$ of testing site was wetted with 10 ml of water delivered with a syringe. The test sample was applied as per FDA monograph C.F.R. 21 to the area. Lather was worked into the subject for 3 minutes to allow the product to absorb into the skin. The area was rinsed after 2 additional minutes with 20 ml of water, then the area was patted dry and allowed 15 minutes before exposure to radiation as per FDA monograph. The skin was exposed to UV radiation and the MED was noted and compared to the MED for skin without treatment. Results are shown in the Table below.

TABLE (Lather Method*)

| Subject ID # | Sex | MED/ Hr | I (Amps) | Skin Type | MED I $J/M^2$ | MED II $J/M^2$ | STD (8% HMS) | SPF Value |
|---|---|---|---|---|---|---|---|---|
| 46 8676 | F | 127.8 | 7.0 | II | 46.20 | 46.20 | 4.40 | 15.00 |
| 50 3379 | F | 126.4 | 7.0 | II | 46.20 | 46.20 | 4.00 | 18.00 |
| 36 0202 | F | 125.8 | 7.0 | II | 46.20 | 46.20 | 4.40 | 21.60 |
| 56 2392 | F | 125.8 | 7.0 | II | 46.20 | 46.20 | 4.00 | 18.00 |
| 50 1415 | F | 125.8 | 7.0 | II | 46.20 | 46.20 | 4.40 | 21.60 |
| MEAN (x) | | | | | | | 4.24 | 18.84 |
| STANDARD DEV (s) | | | | | | | 0.22 | 2.80 |
| STD. ERROR | | | | | | | 0.10 | 1.25 |
| S.E. % OF MEAN | | | | | | | 2.36 | 6.63 |
| N | | | | | | | 5 | 5 |

MED: Minimal Erythemal Dose
I: Intensity of light source

This Example demonstrates that the sunscreen/bodywash enhanced the sun protection as measured by this protocol, as compared to untreated skin, by an average SPF of over 18.

Example 3

A sunscreen/bodywash is prepared by mixing the following ingredients: 0.1 to 7.5 parts by weight of octylmethoxy cinnamate, 0.1 to 6 parts by weight of octyl salicylate, 0.1 to 5 parts by weight of oxybenzone, 1 to 10 parts by weight of cationic surfactant, 0.01 to 1 part by weight of a quaternized compound and 0.01 to 1 part by weight of a preservative.

Example 4

A sunscreen/bodywash is prepared by mixing the following ingredients:
Water 20–65%
Polyquat 4 0.01–3.75%
Dimethicone 0.01–7%
Octylmethoxycinnamate in amorphous silica
Petrolatum 0.01–10%
Titanium Dioxide 0.01–20%
Octocrylene 0.01–10%
Parsol 1789(Avobenzone) 0.01–3%
Kathon 0.01–2%
Bodywash generic 5–99%

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for protection of skin from sunlight, comprising applying a bodywash comprising a sunscreen encapsulated in sol-gel microcapsules to the skin, wherein after application of the bodywash to skin and rinsing, the skin is protected from sunlight with an average SPF of at least about 15.

2. The method of claim 1 comprising applying the bodywash at least twice.

3. The method of claim 2 wherein the average SPF after the second application of bodywash is greater than about 20.

4. The method of claim 1 wherein the bodywash is applied about once per day.

5. The method of claim 1 wherein the bodywash is applied more that about once per day.

6. The method of claim 1 wherein the bodywash is applied about every other day.

7. The method of claim 1, wherein the sunscreen is an organic sunscreen.

8. The method of claim 7, wherein the bodywash further comprises an inorganic sunscreen.

9. The method of claim 8 wherein the bodywash further comprises a cationic polymer.

10. The method of claim 9 wherein the bodywash further comprises a film former.

11. The method of claim 1 wherein the SPF of at least 15 is maintained for at least about 4 hours after rinsing.

12. A method for protection of skin from sunlight, comprising applying the bodywash of claim 1 to the skin, wherein the sunscreen penetrates an average of no further than 30 microns into the skin after application followed by rinsing.

13. The method of claim 12 wherein the sunscreen penetrates an average of no further than 50 microns into the skin after application followed by rinsing.

14. A method for protection of skin from sunlight, comprising applying the bodywash of claim 1 to the skin, wherein the bodywash comprises a UVA-absorbing sunscreen, a UVB-absorbing sunscreen, a physical blocker sunscreen, and a cationic polymer, and wherein at least one of the UVA-absorbing sunscreen and the UVB-absorbing sunscreen is encapsulated in the sol-gel microcapsules.

15. The method of claim 14 wherein the physical blocker sunscreen is coated with silica.

16. The method of claim 14, wherein the cationic polymer is a polyquaternium.

17. The method of claim 14 wherein the bodywash further comprises a film former.

18. The method of claim 14, wherein
(i) the UVB-absorber sunscreen is selected from the group consisting of aminobenzoic acid, cinoxate, dioxyben zone, homosalate, octocrylene, octyl methoxycinnamate, octyl salicylate, oxybenzone, padimate O, phenylbenzimidazole sulfonic acid, sulisobenzone, and trolamine salicylate;

(ii) the UVA-absorber sunscreen is selected from the group consisting of avobenzone and menthyl anthranilate;

(iii) the physical blocker sunscreen is selected from the group consisting of titanium dioxide and zinc oxide; and (iv) the cationic polymer is a polyquaternium.

19. The method of claim 14 wherein the bodywash further comprises a non-sunscreen active.

* * * * *

UNITED STATES PATENT AND TRADEMARK OFFICE
CERTIFICATE OF CORRECTION

| | | |
|---|---|---|
| PATENT NO. | : 7,025,952 B1 | Page 1 of 1 |
| APPLICATION NO. | : 11/076088 | |
| DATED | : April 11, 2006 | |
| INVENTOR(S) | : Traynor et al. | |

It is certified that error appears in the above-identified patent and that said Letters Patent is hereby corrected as shown below:

In the specification at column 34, line 25, please change:

"that" to -- than --

Signed and Sealed this

Fifteenth Day of August, 2006

JON W. DUDAS
*Director of the United States Patent and Trademark Office*